(12) United States Patent
Murakami et al.

(10) Patent No.: US 6,949,926 B2
(45) Date of Patent: Sep. 27, 2005

(54) BIOMAGNETIC MEASUREMENT APPARATUS

(75) Inventors: Masahiro Murakami, Hitachinaka (JP); Hitoshi Sasabuchi, Mito (JP)

(73) Assignee: Hitachi High-Technologies Corporation, Tokyo (JP)

( * ) Notice: Subject to any disclaimer, the term of this patent is extended or adjusted under 35 U.S.C. 154(b) by 282 days.

(21) Appl. No.: 10/456,520

(22) Filed: Jun. 9, 2003

(65) Prior Publication Data

US 2003/0231016 A1 Dec. 18, 2003

(30) Foreign Application Priority Data

Jun. 14, 2002 (JP) ......................................... 2002-173565

(51) Int. Cl.[7] ........................... G01R 33/02; A61B 5/05
(52) U.S. Cl. ....................................... 324/248; 600/409
(58) Field of Search ............................... 324/248, 249, 324/244, 228, 239; 600/409; 326/5; 505/162; 327/366, 367, 370, 527, 528, 551, 559

(56) References Cited

U.S. PATENT DOCUMENTS

| | | | | |
|---|---|---|---|---|
| 5,162,731 A | * | 11/1992 | Fujimaki | 324/248 |
| 6,498,483 B1 | * | 12/2002 | Hirano et al. | 324/248 |
| 6,681,131 B2 | * | 1/2004 | Kandori et al. | 600/409 |
| 6,815,949 B2 | * | 11/2004 | Kandori et al. | 324/248 |
| 2004/0027125 A1 | * | 2/2004 | Clarke et al. | 324/308 |

FOREIGN PATENT DOCUMENTS

JP 9-257895 10/1997

* cited by examiner

*Primary Examiner*—Bot Ledynh
*Assistant Examiner*—Kenneth J Whittington
(74) *Attorney, Agent, or Firm*—Dickstein Shapiro Morin & Oshinsky LLP

(57) ABSTRACT

A biomagnetic measurement apparatus having functions to detect the release of a magnetic field lock in a SQUID fluxmeter operation circuit due to the influence of a much greater noise level than that of a biomagnetic signal, to notify an operator of the release of the magnetic field lock, and to automatically or manually revert to a state for allowing magnetic measurement. The release of the magnetic field lock occurs when an integrator of the fluxmeter operation circuit is saturated. Thus, a high pass filter is provided at a subsequent stage of the integrator, and a function is provided to judge that the integrator is in a saturated state when the noise level of the output after passing through the high pass filter is lower than a pre-set threshold. The biomagnetic measurement apparatus can detect a saturated state of the integrator, which is a cause for the release of the magnetic field lock of the SQUID fluxmeter operation circuit, and thereby when the loading of measured data is conducted in an appropriate operation range of a magnetic sensor, or even when a part of the loaded measured data is data outside an operation range of the magnetic sensor, it is possible to deal with the data so as to properly analyze it.

10 Claims, 6 Drawing Sheets

(A)

Environmental noise output during normal operation (B)

Environmental noise output while magnetic filed lock is released

BIOMAGNETIC MEASUREMENT APPARATUS

BACKGROUND OF THE INVENTION

1. Technical Field

The present invention relates to a biomagnetic measurement apparatus, including a SQUID (Superconducting Quantum Interference Device) fluxmeter that measures weak magnetic signals generated from the heart, the brain, etc. of adults, children, fetuses, or the like. In particular, the present invention relates to the biomagnetic measurement apparatus having means for detecting and avoiding a condition of saturation, when an integrator of a fluxmeter operation circuit is saturated with noise and thereby magnetic measurements cannot be conducted.

2. Background Art

The SQUID fluxmeter has experienced problems such as magnetic field measurement errors, which are caused by changes of output signals of an integrator when phase changes or amplitude changes of amplifier outputs occur due to variations of temperature, power source, or other factors. In order to solve this problem, JP Patent Publication (Kokai) No. 9-257895 A (1997) discloses, in a fluxmeter using SQUID, a magnetometer comprising a comparator that compares an output from a SQUID with preset upper and lower limits. This magnetometer notifies the SQUID or a drive circuit of abnormalities when the output is beyond the upper or lower limits.

In addition to phase changes and amplitude changes of amplifier outputs, which are regarded as problems according to JP Patent Publication (Kokai) No. 9-257895 A (1997), when the SQUID fluxmeter detects further noise greater than a biomagnetic signal, an integrator of a fluxmeter operation circuit becomes saturated and a problem arises wherein a magnetic field lock of a magnetic sensor is released. When the magnetic field lock is released, the output of the fluxmeter does not revert back, even after the causative noise for releasing the lock disappears, and it is impossible to continue the measurement. Therefore, it is necessary to discover that the magnetic field lock is released as early as possible, to notify an operator of the above saturated state (detection of the release of the magnetic field lock), to take required measures to resolve the saturated state, for example, manually or automatically, and to conduct operations for the magnetic field lock again, thereby creating a state for enabling magnetic measurements.

SUMMARY OF THE INVENTION

An object of the present invention is to provide a biomagnetic measurement apparatus having a function to detect the release of a magnetic field lock.

In order to solve the above problems, the present invention has the following configuration.

A biomagnetic measurement apparatus comprises: at least one magnetic sensor having a superconducting quantum interference device (SQUID) that detects a magnetic field generated from a subject to be tested; a cryostat for holding the SQUID at a low temperature; a fluxmeter operation circuit of the SQUID; and a computer for colleting an output signal of the fluxmeter operation circuit. The fluxmeter operation circuit comprises: an integrator for integrating an magnetic signal output detected by the SQUID; a filter for removing a direct-current component from the output of the integrator; and lock release detection means for detecting the release of the magnetic field lock by judging whether the output of the integrator that has been passed through the filter is substantially zero.

The filter for removing a direct-current component may be a filter commonly referred to as a high pass filter. The phrase "the output of the integrator is substantially zero" means that there is almost no output except a small amount of noise occasionally generated from an amplifier, etc. It also means an output which becomes almost zero when the output is integrated. Likewise, when a threshold has been previously set, the state wherein the release of the magnetic field lock occurs can be detected by monitoring whether the output is not greater than the pre-set threshold.

When the release of the magnetic lock occurs, the data measured after the occurrence of the release becomes invalid. Therefore, it is preferable that the apparatus be provided with a means for notifying an apparatus operator of the occurrence, so as to urge the operator to take appropriate measures. As a means for notification, in the case of a device that operates the apparatus by a PC, etc. provided with an operation screen such as a CRT screen, an indication on the operation screen, which gives notice when the release of the magnetic field lock occurs, may be used. Alternatively, an alarm may be used. As long as the operator can recognize the release of the magnetic field lock, any means can be used.

After the release of the magnetic field lock occurs, a system may be used that locks the apparatus, to prevent the apparatus from conducting biomagnetic measurement. Alternatively, a system that automatically cancels the release of the lock may be provided in the apparatus. In such case, unless the operator recognizes the occurrence of the lock release, there is a possibility that invalid measured data could be considered valid and used for analysis. Thus, it is preferable to display on the measured data when the release of the magnetic field lock occurred, when the lock release was cancelled, or both.

DESCRIPTION OF THE PREFERRED EMBODIMENT

Embodiments of the present invention will be described using figures.

Figure 1:
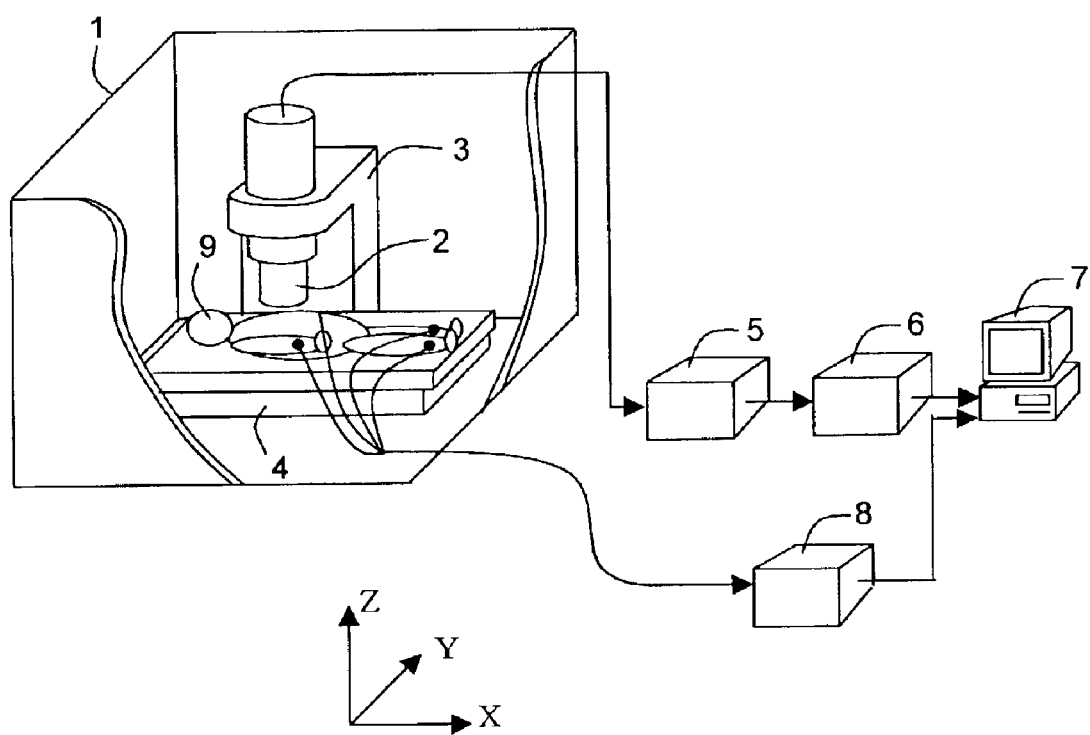
FIG. 1 is a view showing a configuration of a biomagnetic measurement apparatus according to an embodiment of the present invention.

FIG. 1 is a view showing a configuration of a biomagnetic measurement apparatus according to an embodiment of the present invention. As shown in FIG. 1, inside a magnetic shield room 1, there are disposed a bed 4 on which a subject being tested lies down, plural (plural channels) SQUID magnetic sensors, a cryostat 2 which stores refrigerants (liquid helium or liquid nitrogen) for keeping the SQUID magnetic sensors in a superconductive state, and a gantry 3 for mechanically holding the cryostat 2. The bed 4 is movable in the directions of X, Y, and Z axes. Outside the magnetic shield room 1, a SQUID fluxmeter operation circuit 5, a unit 6 of an amplifier circuit and a filter circuit, a computer 7 for data loading and data analysis, and circuit 8 for taking external reference signals such as those from an electrocardiograph are arranged.

A biomagnetic signal detected by the SQUID magnetic sensor is amplified by the unit 6 of the amplifier and filter circuits and is passed through a signal processing means such as a low pass filter for enabling a lower frequency signal than that of the setting frequency to pass through, a high pass filter for enabling a higher frequency signal than that of the setting frequency to pass through, and a notch filter for removing only the frequencies of commercial power sources. Thereafter, the signal is loaded into the computer 7 as raw data. Further, the waveform of a signal from the circuit 8 for taking external reference signals such as an electrocardiograph is loaded into the computer 7 as raw data. Furthermore, the computer 7 stores the loaded raw data in a raw data file and displays the waveform on a screen, and also performs a signal processing of the waveform and displays the results thereof.

Figure 2:
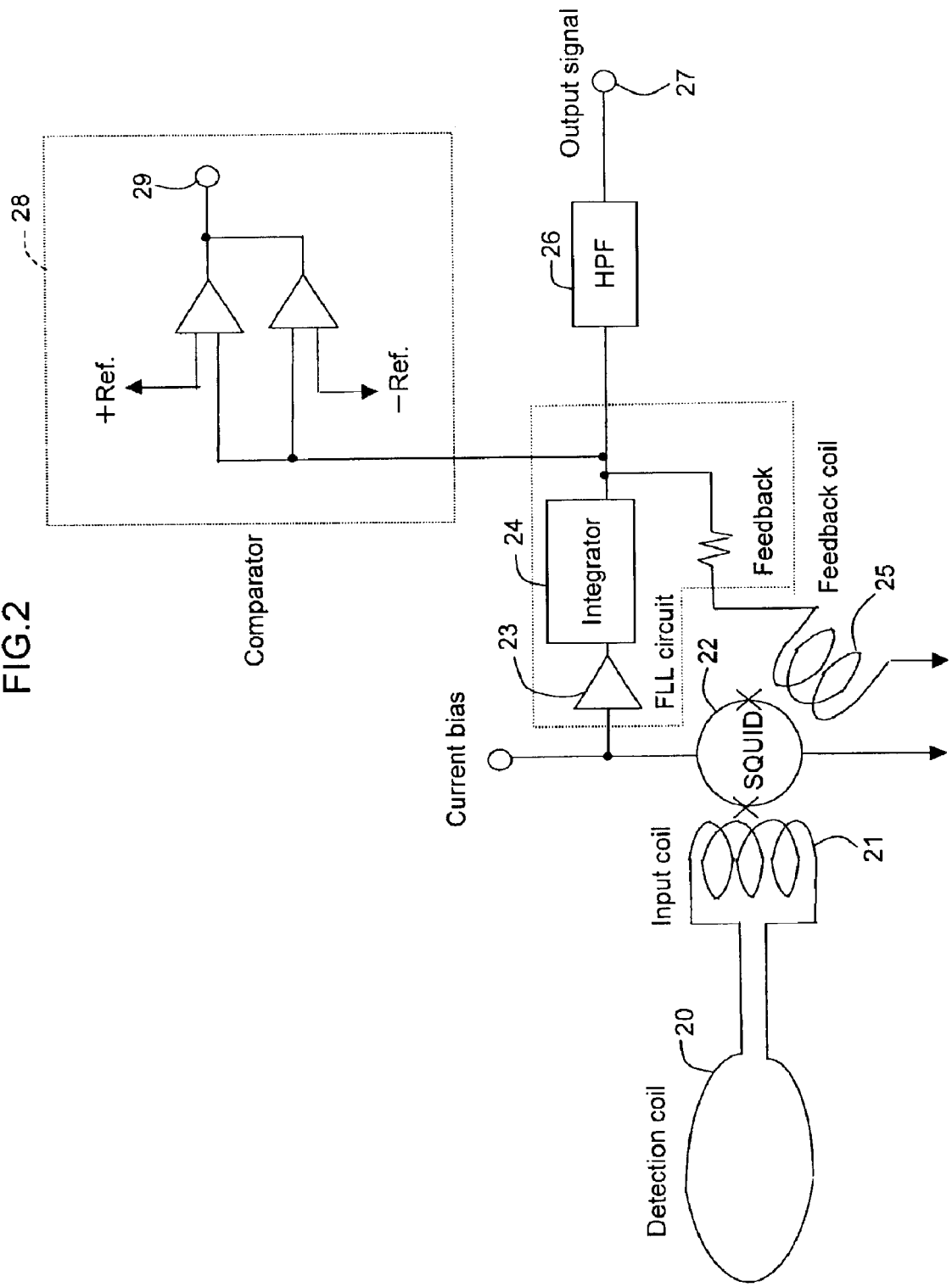
FIG. 2 is a view showing a circuit configuration of a SQUID fluxmeter of the biomagnetic measurement apparatus according to the embodiment of the present invention.

FIG. 2 is a view showing a circuit configuration of the SQUID fluxmeter of the biomagnetic measurement apparatus according to the embodiment of the present invention. The SQUID magnetic sensor described above by referring to FIG. 1 comprises a detection coil 20, an input coil 21, and a superconductive ring 22. The biomagnetic signal captured by the detection coil 20 is transmitted through the input coil 21 as a magnetic flux passing through the superconductive ring 22. The output signal voltage of the superconductive ring 22 obtained by the magnetic flux passing through the superconductive ring 22 is amplified by a preamplifier 23, and then integrated and outputted by an integrator 24. Further, the output voltage is given with a feedback circuit and a feedback coil 25 as negative feedback toward changes of the magnetic flux passing through the superconductive ring 22. Thus, the magnetic flux passing the superconductive ring can be kept constant, and the impact of the circuit for amplifying signals or the impact of nonlinearity and drift can be reduced. A feedback group including the feedback circuit and a feedback coil 25 is generally referred to as a Flux Locked Loop (FLL).

When a comparator circuit 28 is arranged directly after the integrator 24, it is detectable if the integrator 24 is saturated with further magnetic noises greater than biomagnetic signals. However, whether or not the saturated state causes the release of the magnetic field lock cannot be recognized by the comparator. Therefore, in the present invention, a high pass filter 26 is provided directly after the integrator 24. By judging whether the output signal of the high pass filter is almost zero, or, when a subtle threshold is set, whether the output signal is not greater than the threshold, the occurrence of the release of the magnetic field lock can be detected. In this case, when the release of the magnetic field lock occurs, the direct-current component is removed from the output signal of the integrator 24 by the high pass filter 26. Hence, the output signal 27 directly after passing through the high pass filter 26 has a smaller output than the noise output of an ordinary environment (shown in FIG. 3).

Figure 3:
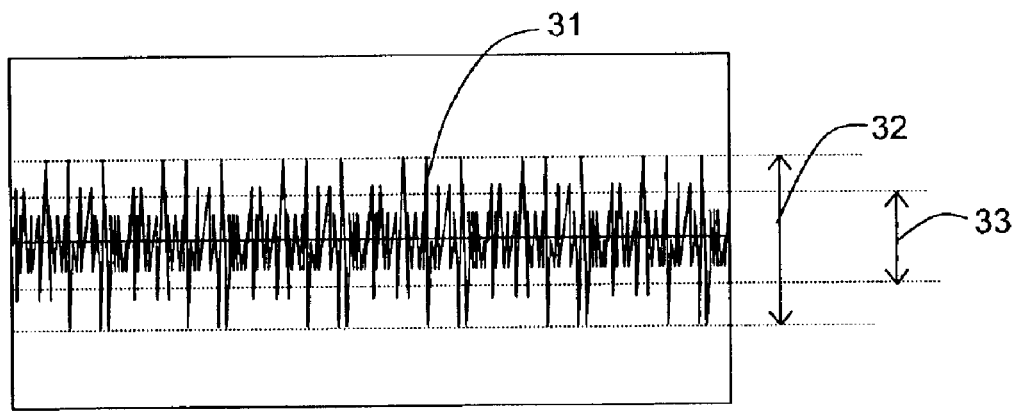
FIG. 3 is a view, with respect to the output signal 27 of FIG. 2, showing an environmental noise output waveform 31 (FIG. 3(A)) during a normal time and an environmental noise output waveform 34 (FIG. 3(B)) at a time when the release of the magnetic field lock occurs in the fluxmeter operation circuit due to a high noise level.
Figure 3:
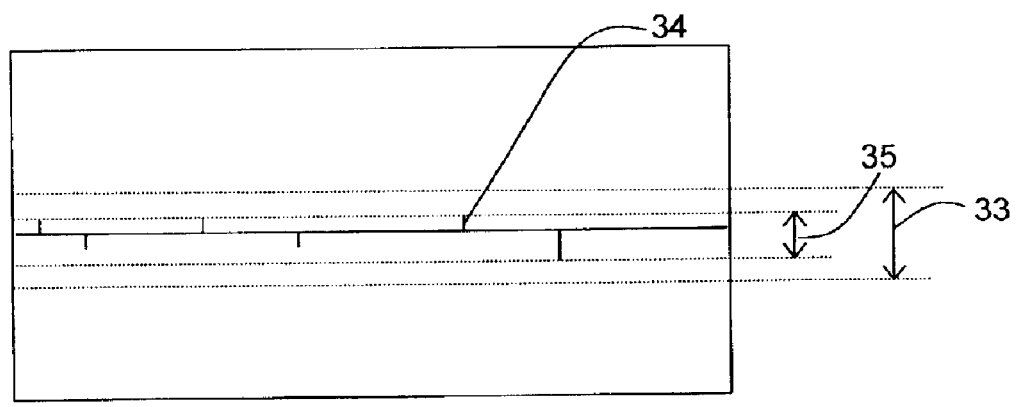

FIG. 3 is a view, with respect to the output signal 27 of FIG. 2, showing an environmental noise output waveform 31 (FIG. 3(A)) during a normal time and an environmental noise output waveform 34 at a time when the release of the magnetic field lock occurs in the fluxmeter operation circuit due to a high noise level. The waveform amplitude 35 of the output waveform 34 (FIG. 3(B)) is nearly zero in comparison with the waveform amplitude 32 of the output waveform 31, and thus the occurrence of the release of the magnetic field lock can be judged by setting a threshold width 33 of the amplitude. Further, as a judgment condition, the integral of an absolute value of the waveform amplitude during a given period may be used.

Figure 4:
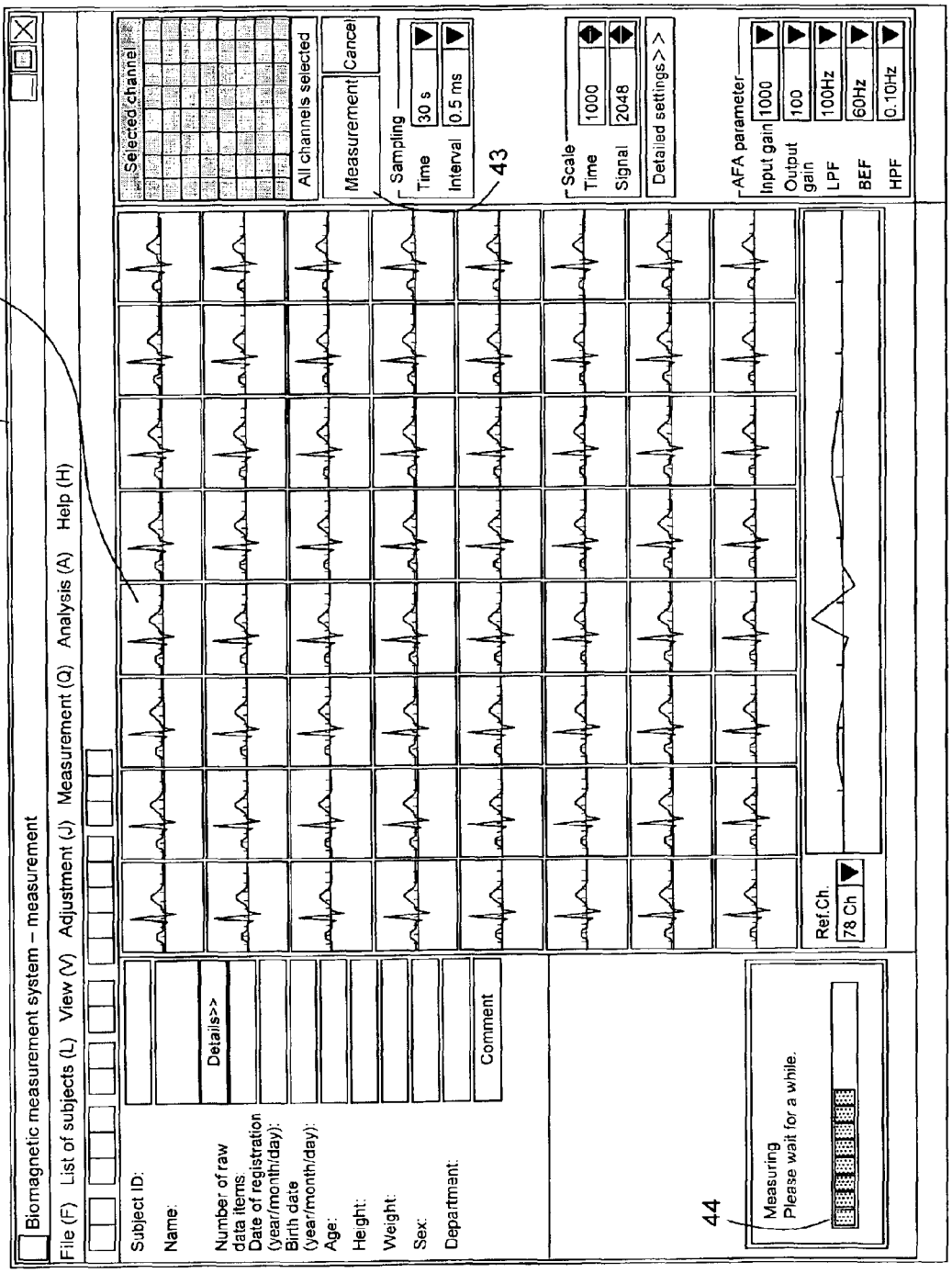
FIG. 4 is a view showing one example of a measurement screen using biomagnetic measurement software according to the embodiment of the present invention.

FIG. 4 is a view showing one example of a measurement screen using biomagnetic measurement software according to the embodiment of the present invention. On a measurement screen 41, a biomagnetic signal waveform 42 measured by a magnetic sensor at each channel is displayed. FIG. 4 shows one example wherein the waveforms for 64 channels are displayed on one screen, but it is possible to display the waveforms for only selected channels. When a measurement start button 43 is clicked, the loading of magnetic signal waveform data starts. The progress from the start to the end of data loading is indicated on an indicator 44.

Figure 5:
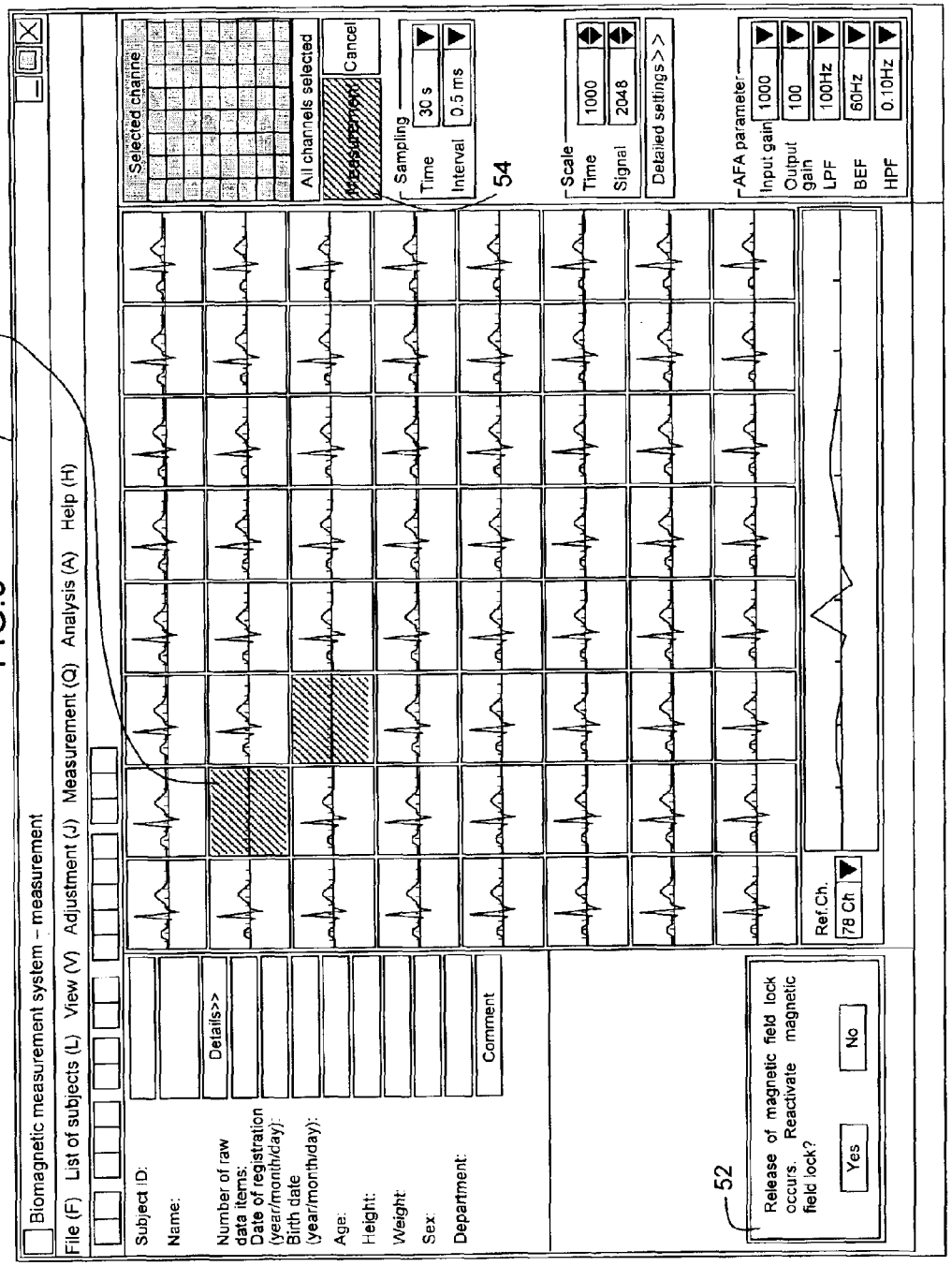
FIG. 5 is a view showing one example of a measurement screen using biomagnetic measurement software according to the embodiment of the present invention.

FIG. 5 is a view showing one example of a measurement screen using biomagnetic measurement software according to the embodiment of the present invention. When the release of the magnetic field lock (saturated state of the integrator of the fluxmeter) is detected before starting to load magnetic signal waveform data, the color of waveform windows 53 for channels each having the release of the magnetic field lock is changed on a measurement screen 51 to inform an operator of the occurrence of the release. Further, an error message box 52 is displayed to give notification that the release of the magnetic field lock has occurred. Then, for reactivating the magnetic field lock, a [Yes] button in the error message box 52 is to be clicked. Furthermore, in order to prevent the data loading from starting during the release of the magnetic field lock, the color of the measurement start button 54 is changed and clicking the button is impossible.

Figure 6:
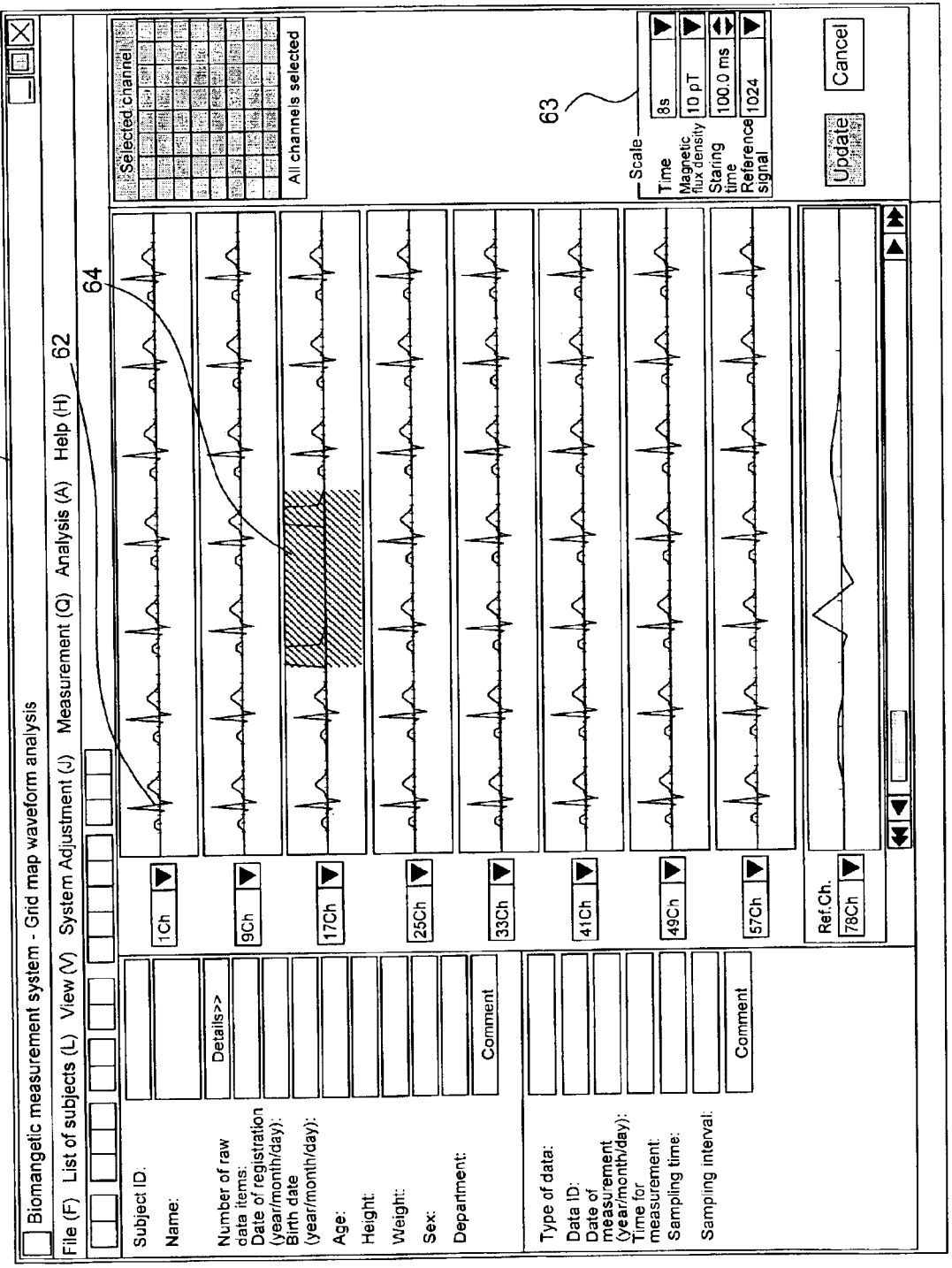
FIG. 6 is a view showing one example of a waveform analysis screen using biomagnetic measurement software according to the embodiment of the present invention.

FIG. 6 is a view showing one example of a waveform analysis screen using biomagnetic measurement software according to the embodiment of the present invention. FIG. 6 shows one example wherein the waveforms for 8 channels are displayed on one screen, but it is possible to display the waveforms for only selected channels. On a waveform analysis screen 61, a biomagnetic signal waveform 62 measured by a magnetic sensor of each channel is displayed. Through a display setting input box 63, it is possible to conduct scale settings for a time axis or magnetic field strength. In addition, when the release of the magnetic field lock occurs during the measured data loading, the part of the measured data on which the release of the magnetic field lock occurs can be displayed as an indication 64. When the biomagnetic measurement apparatus automatically cancels the release of the magnetic field lock, the time period in which the release of the magnetic field lock has occurred is displayed in the same manner as the indication 64. The time period of the indication 64 can be set so as to represent not only the period from the time when the release of the magnetic field lock is detected to the time the release of the magnetic field lock is cancelled (lifted), but the time that includes, in addition to the above, an enlarged range by taking the time constant of the circuit into account to differentiate it from the measured data valid for analysis.

This application is based on the Japanese patent application 2002-173565, all the contents of which is incorporated in this application by reference.

EFFECT OF THE INVENTION

The present invention described above provides a biomagnetic measurement apparatus that can detect a saturated state of an integrator of a biomagnetic measurement apparatus, which is a cause for the release of a magnetic field lock in a SQUID fluxmeter operation circuit. Therefore, when the loading of measured data is conducted in an appropriate operation range of a magnetic sensor, or even when a part of the loaded measured data is data outside an operation range of the magnetic sensor, it is possible to deal with the data so as to properly analyze it.

What is claimed is:

1. A biomagnetic measurement apparatus comprising:
   at least one magnetic sensor having a superconducting quantum interference device (SQUID) that detects a magnetic field generated from a subject to be tested;
   a cryostat for holding the SQUID at a low temperature;
   a fluxmeter operation circuit of the SQUID; and
   a computer for collecting an output signal of the fluxmeter operation circuit,
   wherein the fluxmeter operation circuit comprises:
   an integrator for integrating a magnetic field signal output detected by the SQUID;
   a filter for removing a direct-current component from the output of the integrator; and
   lock release detection means for detecting the release of the magnetic field lock by judging whether the output of the integrator that has been passed through the filter is substantially zero.

2. The biomagnetic measurement apparatus according to claim 1,
   wherein the apparatus comprises means for giving notification of measurement impossibility when the lock release detection means detects the release of the magnetic field lock.

3. The biomagnetic measurement apparatus according to claims 1,
   wherein the apparatus comprises means for preventing biomagnetic measurement from starting when the lock release detection means detects the release of the magnetic field lock.

4. The biomagnetic measurement apparatus according to claims 1,
   wherein the apparatus comprises means for creating a state for allowing measurement by automatically resolving a saturated state of the integrator and for continuing the measurement when the lock release detection means detects the release of the magnetic field lock.

5. The biomagnetic measurement apparatus according to claim 4,
   wherein the apparatus comprises means for displaying on measured data a time when the lock release occurs and a time when the apparatus reverts to the state for allowing the measurement.

6. A biomagnetic measurement apparatus comprising:
   at least one magnetic sensor having a superconducting quantum interference device (SQUID) that detects a magnetic field generated from a subject to be tested;
   a cryostat for holding the SQUID at a low temperature;
   a fluxmeter operation circuit of the SQUID; and
   a computer for collecting an output signal of the fluxmeter operation circuit,
   wherein the fluxmeter operation circuit comprises:
   an integrator for integrating a magnetic field signal output detected by the SQUID;
   a filter for removing a direct-current component from the output of the integrator; and
   lock release detection means for detecting the release of the magnetic field lock by judging whether the output of the integrator which has been passed through the filter has a lower noise level than a pre-set threshold.

7. The biomagnetic measurement apparatus according to claim 6,
   wherein the apparatus comprises means for giving notification of measurement impossibility when the lock release detection means detects the release of the magnetic field lock.

8. The biomagnetic measurement apparatus according to claims 6,
   wherein the apparatus comprises means for preventing biomagnetic measurement from starting when the lock release detection means detects the release of the magnetic field lock.

9. The biomagnetic measurement apparatus according to claims 6,
   wherein the apparatus comprises means for creating a state for allowing measurement by automatically resolving a saturated state of the integrator and for continuing the measurement when the lock release detection means detects the release of the magnetic field lock.

10. The biomagnetic measurement apparatus according to claim 9,
    wherein the apparatus comprises means for displaying on measured data a time when the lock release occurs and a time when the apparatus reverts to the state for allowing the measurement.

* * * * *